(12) United States Patent
Fuerstenberg et al.

(10) Patent No.: US 11,105,796 B2
(45) Date of Patent: Aug. 31, 2021

(54) METHODS FOR NON-INVASIVE PROFILING OF STEM CELL DIFFERENTIATION

(71) Applicant: Bio-Techne Corporation, Minneapolis, MN (US)

(72) Inventors: Richard Karl Fuerstenberg, St. Paul, MN (US); Joy Lynn Aho, Maple Grove, MN (US); Fabrizio Rinaldi, Minneapolis, MN (US)

(73) Assignee: BIO-TECHNE CORPORATION, Minneapolis, MN (US)

( * ) Notice: Subject to any disclaimer, the term of this patent is extended or adjusted under 35 U.S.C. 154(b) by 587 days.

(21) Appl. No.: 15/622,937

(22) Filed: Jun. 14, 2017

(65) Prior Publication Data

US 2017/0363617 A1   Dec. 21, 2017

Related U.S. Application Data

(60) Provisional application No. 62/352,752, filed on Jun. 21, 2016.

(51) Int. Cl.

| | |
|---|---|
| *G01N 33/50* | (2006.01) |
| *A61K 35/12* | (2015.01) |
| *A61K 39/395* | (2006.01) |
| *C12N 5/10* | (2006.01) |
| *C12N 5/0735* | (2010.01) |
| *C12Q 1/06* | (2006.01) |
| *C12N 5/077* | (2010.01) |
| *C12N 5/074* | (2010.01) |
| *C12N 5/071* | (2010.01) |
| *G01N 33/68* | (2006.01) |
| *A61K 48/00* | (2006.01) |

(52) U.S. Cl.
CPC ......... *G01N 33/5073* (2013.01); *A61K 35/12* (2013.01); *A61K 39/395* (2013.01); *C12N 5/0606* (2013.01); *C12N 5/067* (2013.01); *C12N 5/0657* (2013.01); *C12N 5/0696* (2013.01); *C12N 5/10* (2013.01); *C12Q 1/06* (2013.01); *G01N 33/5005* (2013.01); *G01N 33/6863* (2013.01); *A61K 48/00* (2013.01)

(58) Field of Classification Search
CPC ...... A61K 35/12; A61K 39/395; A61K 48/00; C12N 5/0606; C12N 5/0657; C12N 5/067; C12N 5/0696; C12N 5/10; C12Q 1/06; G01N 33/5005; G01N 33/5073; G01N 33/6863

See application file for complete search history.

(56) References Cited

U.S. PATENT DOCUMENTS

| | | | |
|---|---|---|---|
| 2003/0153013 A1* | 8/2003 | Huang | G01N 33/6842 435/7.9 |
| 2011/0045606 A1* | 2/2011 | Kennedy | G01N 33/538 436/501 |
| 2013/0071931 A1* | 3/2013 | Ishikawa | C12N 5/067 435/377 |
| 2013/0309245 A1* | 11/2013 | Lombardi | G01N 33/6869 424/158.1 |
| 2015/0368713 A1* | 12/2015 | Bharti | C12N 5/0621 506/9 |

OTHER PUBLICATIONS

Amable et al., "Gene expression and protein secretion during human mesenchymal cell differentiation into adipogenic cells," BMC Cell Biology, vol. 15, 2014, 10 pages.

* cited by examiner

*Primary Examiner* — Blaine Lankford
(74) *Attorney, Agent, or Firm* — Mueting Raasch Group

(57) ABSTRACT

A method for characterizing stem cell differentiation includes harvesting differentiation media supernatant containing secreted analytes from key time points during a stem cell differentiation, performing at least one of a qualitative and a quantitative analysis of the differentiation media supernatant with respect to at least one secreted analyte, and identifying trends in analyte expression based on at least one of the qualitative and quantitative analysis of the differentiation media supernatant.

20 Claims, 14 Drawing Sheets

METHODS FOR NON-INVASIVE PROFILING OF STEM CELL DIFFERENTIATION

CROSS-REFERENCE

This application claims priority to U.S. patent application Ser. No. 62/352,752, filed Jun. 21, 2016, the entire contents of which are incorporated by reference herein.

TECHNICAL FIELD

This disclosure relates to methods for profiling stem cell differentiation, and more particularly, methods for non-invasive characterization of stem cell differentiation

BACKGROUND

Stem cells, particularly pluripotent stem cells, have the potential to revolutionize medicine. Stem cells are useful in many applications, including treatment of heart disease, repair of spinal cords and treatment of many other diseases where tissues of all kinds need to be replaced. To fully realize the potential of stem cells, robust and standardized stem cell differentiation and characterization protocols are necessary. Characterization of stem cell differentiation generally involves expression profiling of key markers characteristic of the cell type of interest. Current methods for characterization of stem cell differentiation, such as reverse transcription polymerase chain reaction (rt-PCR), Western blotting, flow cytometry, and immunocytochemistry, involve lysing or fixing the cell population of interest. These methods do not allow for analysis at intermediate stages of differentiation with continued culture afterwards.

SUMMARY

In general, this disclosure relates to non-invasive methods for evaluating stem cell differentiation. During differentiation, stem cells secrete analytes, such as cytokines and growth factors, into the cell culture media in which the stem cells are differentiating. Supernatant samples containing analytes for analysis are taken from the culture media at key intermediate stages of differentiation. The disclosed methods thus eliminate the need to lyse or fix the cell population of interest in order to characterize cell differentiation, allowing for analysis of intermediate stages of cell differentiation within a single cell culture.

In one embodiment, a method for characterizing stem cell differentiation includes harvesting differentiation media supernatant containing secreted analytes from key time points during a stem cell differentiation, performing at least one of a qualitative and a quantitative analysis of the differentiation media supernatant with respect to at least one secreted analyte, and identifying trends in analyte expression based on at least one of the qualitative and quantitative analysis of the differentiation media supernatant.

In another embodiment, a method for characterizing stem cell differentiation includes harvesting differentiation media supernatant containing secreted analytes from key time points during a stem cell differentiation of a pluripotent stem cell into a hepatocyte-like cell or a cardiomyocyte, performing at least one of a qualitative and a quantitative analysis of the differentiation media supernatant with respect to at least one secreted analyte, and identifying trends in analyte expression based on at least one of the qualitative and quantitative analysis of the differentiation media supernatant.

In another embodiment, a method for characterizing stem cell differentiation includes harvesting differentiation media supernatant containing secreted analytes from key time points during a stem cell differentiation, performing a qualitative analysis of the differentiation media supernatant with respect to at least one secreted analyte, identifying at least one analyte of interest, performing a quantitative analysis of the differentiation media with respect to the at least one analyte of interest, and identifying trends in analyte expression based on at least one of the qualitative and quantitative analysis of the differentiation media supernatant.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the disclosure in any way. Rather, the following description provides some practical illustrations for implementing examples of the present disclosure. Examples of constructions, materials, dimensions, and manufacturing processes are provided for selected elements, and all other elements employ that which is known to those of ordinary skill in the field of the disclosure. Those skilled in the art will recognize that many of the noted examples have a variety of suitable alternatives.

Figure 1A:
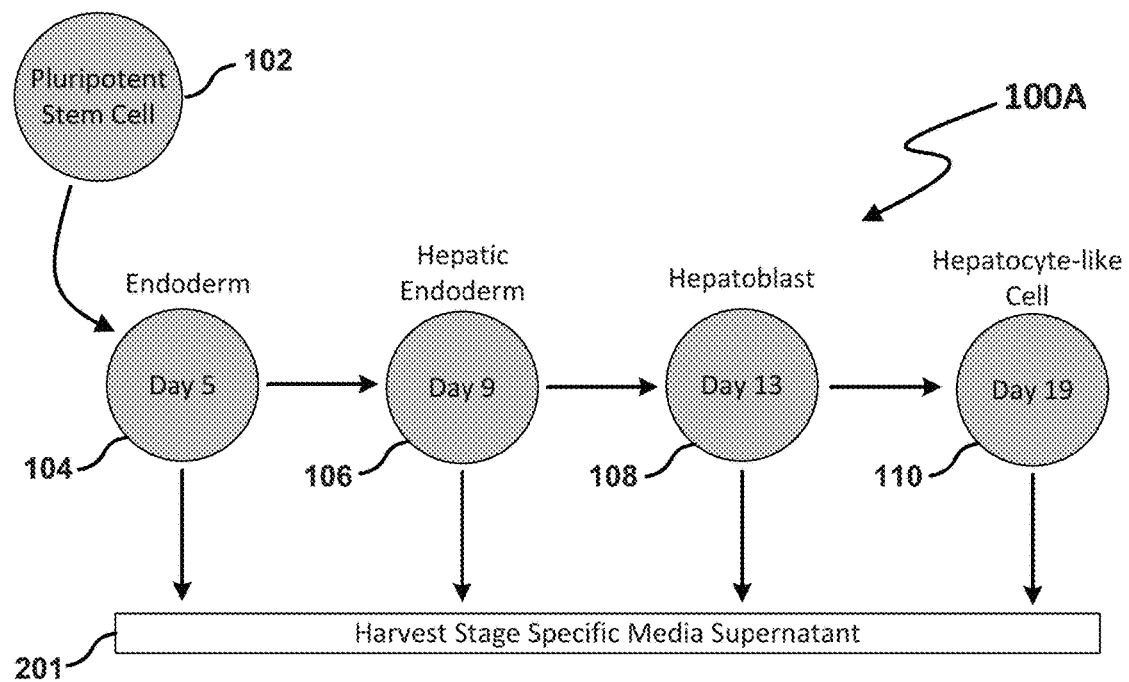
FIG. 1A is a flow diagram illustrating key stages in an example differentiation of a pluripotent cell into a hepatocyte-like cell.

FIG. 1A is a flow diagram illustrating key stages in example differentiation 100A of a pluripotent cell into a hepatocyte-like cell. Differentiation 100A may be carried out using, for example, the StemXVivo® Hepatocyte Differentiation Kit. Differentiation 100A includes pluripotent stem cell 102, endoderm 104, hepatic endoderm 106, hepatoblast 108, and hepatocyte-like cell 110. Pluripotent stem cell 102 can be an induced pluripotent stem cell or an embryonic stem cell. Differentiation 100A takes approximately 19 days to differentiate pluripotent stem cell 102 into hepatocyte-like cell 110. During example differentiation 100A, pluripotent stem cell 102 differentiates into endoderm 104 by day 5, into hepatic endoderm 106 by day 9, into hepatoblast 108 by day 13, and into hepatocyte-like cell 110 by day 19.

To initiate differentiation 100A, pluripotent stem cell 102 is plated into expansion media to allow pluripotent stem cell 102 to grow at least one day prior to initiating differentiation. On day 0 of differentiation 100A, pluripotent stem cell 102 is transferred to differentiation media. During differentiation, stem cells secrete analytes, such as cytokines and growth factors, into the differentiation media. These analytes are extracellular signaling molecules that mediate cell to cell communication. On day 5, when pluripotent stem cell 102 has differentiated into endoderm 104, the spent differentiation media supernatant containing secreted analytes is harvested and frozen. The differentiation media is replenished, and endoderm 104 continues to differentiate. On day 9, when endoderm 104 has differentiated into hepatic endoderm 106, the spent differentiation media supernatant is again harvested and frozen, and the differentiation media is replenished. This procedure is carried out again on day 13 with hepatoblast 108, and on day 19 with hepatocyte-like cell 110.

Figure 1B:
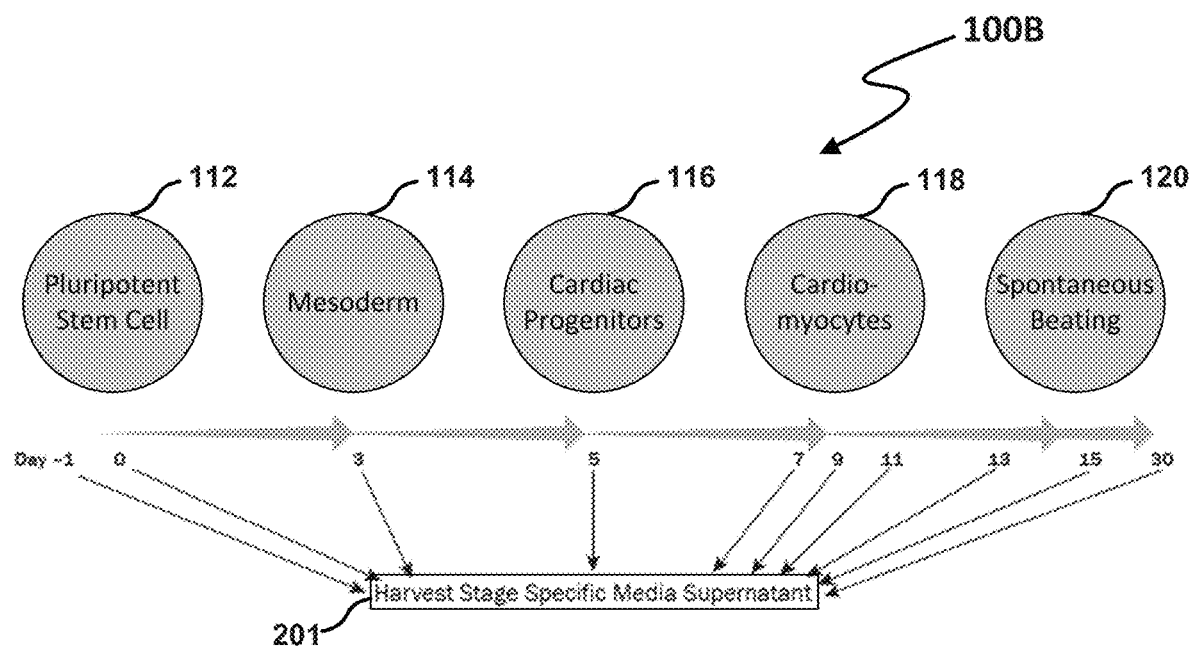
FIG. 1B is a flow diagram illustrating key stages in an example differentiation of a pluripotent stem cell into a cardiomyocyte.

FIG. 1B is a flow diagram illustrating key stages in example differentiation 100B of a pluripotent cell into a cardiomyocyte. Differentiation 100B may be carried out using, for example, the StemXVivo® Cardiomyocyte Differentiation Kit. Differentiation 100B includes pluripotent stem cell 112, mesoderm 114, cardiac progenitor 116, cardiomyocytes 118, and spontaneous beating cells 120. Pluripotent stem cell 112 can be an induced pluripotent stem cell or an embryonic stem cell. Differentiation 100B takes approximately 13-30 days to differentiate pluripotent stem cell 112 into spontaneous beating cells 120. During example differentiation 100B, pluripotent stem cell 112 differentiates into mesoderm 114 by day 3, into cardiac progenitors 116 by day 5, into cardiomyocytes 118 by days 7-11, and into spontaneous beating cardiomyocytes 120 by days 13-30. When cardiac progenitors differentiate 116 start to beat, this is an indication that they have differentiated into cardiomyocytes 118. When cardiomyocytes 118 further differentiate, more cells start to beat, thus becoming spontaneous beating cardiomyocytes 120.

To initiate differentiation 100B, pluripotent stem cell 112 is plated into expansion media to allow pluripotent stem cell 112 to grow at least one day (Day −1) prior to initiating differentiation. On day 0 of differentiation 100B, pluripotent stem cell 112 is transferred to differentiation media. During differentiation, stem cells secrete analytes, such as cytokines and growth factors, into the differentiation media. These analytes are extracellular signaling molecules that mediate cell to cell communication. On day 3, when pluripotent stem cell 112 has differentiated into mesoderm 114, the spent differentiation media supernatant containing secreted analytes is harvested and frozen. The differentiation media is replenished, and mesoderm 114 continues to differentiate. On day 5, when mesoderm 114 has differentiated into cardiac progenitors 116, the spent differentiation media supernatant is again harvested and frozen, and the differentiation media is replenished. This procedure is carried out again on days 7, 9, and 11 with cardiomyocytes 118, and on days 13, 15, and 30 with spontaneous beating cells 120.

As shown in FIGS. 1A and 1B, throughout example differentiations 100A and 100B, cell culture media supernatant is harvested from each key stage of the differentiation (201). This is the first step in the non-invasive stem cell differentiation profiling methods of this disclosure. The methods of this disclosure are not limited to differentiation of pluripotent stem cells into hepatocyte-like cells or cardiomyocytes. In other examples, the methods of this disclosure are applicable to differentiation of pluripotent stem cells, including induced pluripotent stem cells and embryonic stem cells, into neural lineage cells, pancreatic cells and other lineage specific cells. Depending on the cell lineage, key stages of differentiation may occur at different times. Thus, different days may be chosen accordingly for harvesting the differentiation media supernatant.

Figure 2A:
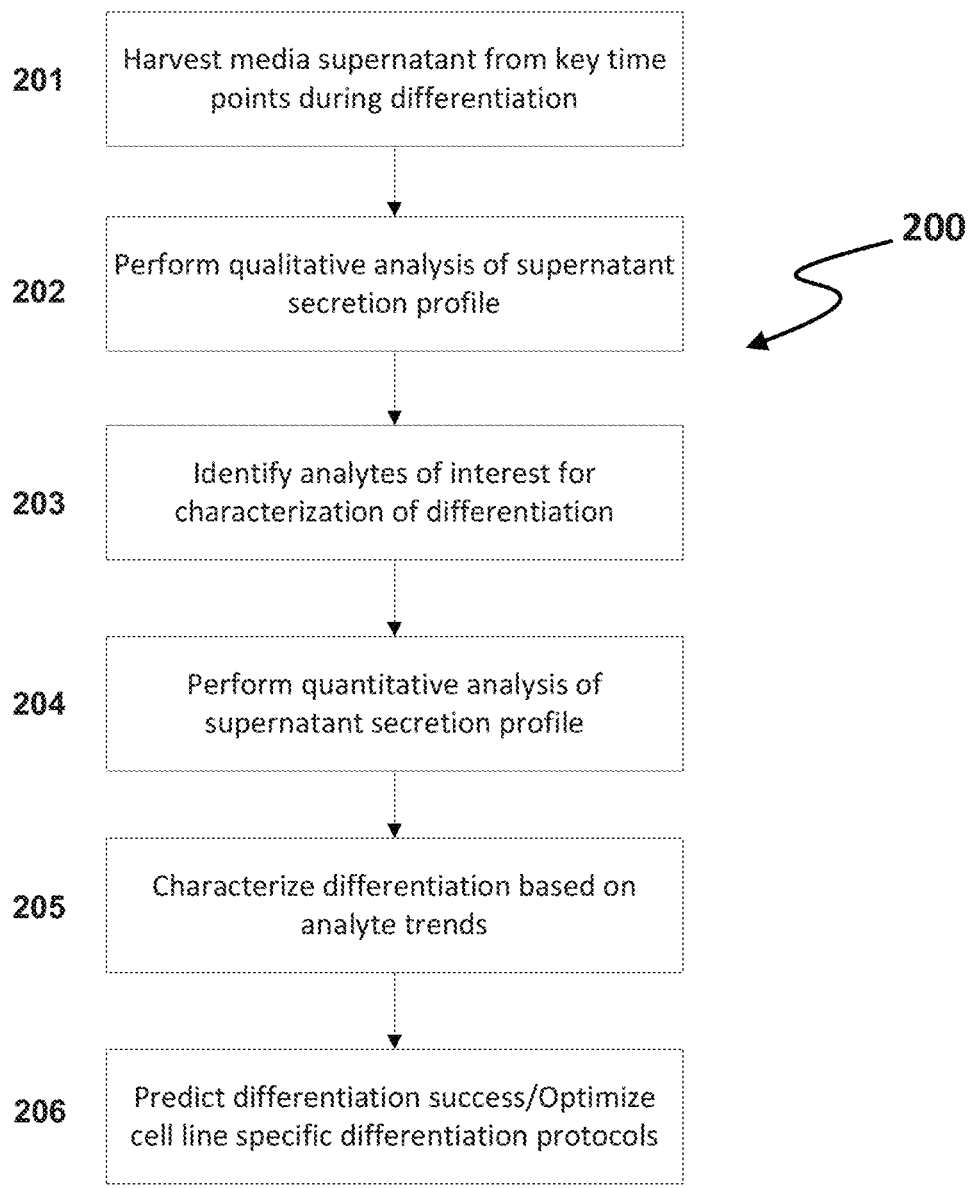
FIG. 2A is a flow diagram illustrating an example of a non-invasive stem cell differentiation profiling method according to this disclosure.

FIG. 2A is a flow diagram of non-invasive stem cell differentiation profiling method 200. Method 200 includes harvesting stage specific media supernatant (201) from each key stage of a differentiation, such as example differentiations 100A and 100B, for analysis. Because analytic samples are obtained from the culture media, the cells are able to continue through the differentiation process, allowing samples from key stages of the same culture to be analyzed to characterize the differentiation. This is advantageous, because current methods of characterization of stem cell differentiation do not allow for analysis of key intermediate stages with continued culture afterwards.

The method of characterization of cell culture supernatants of this disclosure can be used to optimize differentiation protocols by comparing supernatants from successful and failed differentiations. These analyses can assist in optimizing differentiation protocols, including identification of analytes indicative of successful differentiation, identification of analytes that could assist in enhancing differentiation and/or maturation of differentiated cells, and determining the key to turning failed differentiations into successful differentiations. Additionally, analyzing the supernatant allows for analysis of a cell population resulting from a differentiation without having to lyse or fix the cells for analysis, which could be instrumental in controlling the quality of differentiated cells prior to use of those cells in therapeutics.

Method 200 can include harvesting media supernatant from key time points during a differentiation protocol (201), performing qualitative analysis of a secretion profile obtained from the cell culture supernatant (202), identifying analytes of interest for characterization of the differentiation protocol (203), performing quantitative analysis of the secretion profile obtained from the cell culture supernatant (204), characterizing the differentiation based on trends observed in the analytes of interest (205), and predicting differentiation success/optimizing cell line specific differentiation protocols based on the observed trends (206). The steps of method 200 are not limited to the order shown in FIG. 2A. In some examples, only qualitative analysis (202) is performed. In other examples, only quantitative analysis (204) is performed. In other examples, qualitative analysis (202) and quantitative analysis (204) are performed in parallel.

As described above with respect to FIG. 1, differentiation cell media supernatant is harvested (201) from each key differentiation stage and frozen until the differentiation is complete. Once the supernatant from each stage in the differentiation has been collected, qualitative analysis can be performed to analyze the secretion profile (202). In one example, an antibody-based array kit, such as the Proteome Profiler™ XL Cytokine Array Kit, may be used to perform the qualitative analysis. In other examples, other suitable qualitative analysis methods, such as lateral flow immunoassay, may be used. Qualitative methods allow for simultaneous analysis of a high volume of analytes in the supernatant samples. This provides an efficient way to identify analytes of interest for characterization of a differentiation.

Figure 2B:
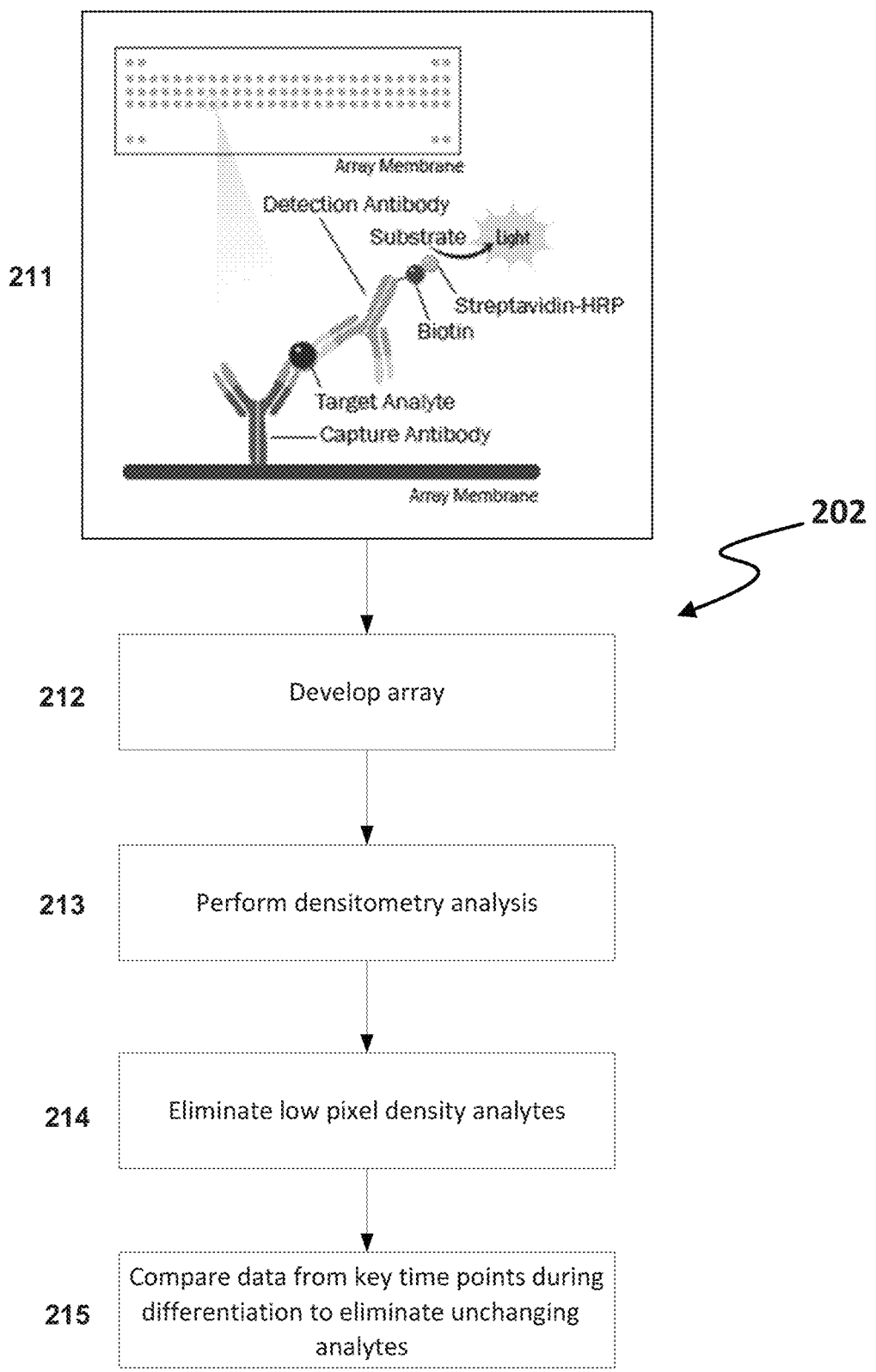
FIG. 2B is a flow diagram illustrating an example qualitative analysis method for analyzing supernatant secretion profiles, used in the non-invasive profiling method of FIG. 2A.

FIG. 2B is a flow diagram illustrating qualitative analysis method 202 for analyzing supernatant secretion profiles. In the example shown in FIG. 2B, qualitative analysis method 202 is performed using the Proteome Profiler™ XL Cytokine Array Kit, which allows for parallel determination of relative levels of 102 human soluble proteins, including cytokines, chemokines, growth factors, and other soluble proteins. Qualitative analysis method 202 includes performing the array protocol for supernatant samples from each key time point during the differentiation (211), developing the array (212), performing densitometry analysis on the array (213), eliminating low pixel density analytes (214), and comparing data from key time points during differentiation to eliminate unchanging analytes.

To perform the array protocol (211), supernatant samples from each key time point are added to a separate nitrocellulose membrane. Each membrane includes 102 capture and control antibodies spotted in duplicate. The 102 capture and control antibodies correspond to 102 different analytes (human soluble proteins). In some examples, the supernatant samples can be diluted prior to addition to each membrane. In other examples, the supernatant samples are not diluted prior to addition to each membrane. Once the samples are added to each membrane, the membranes are incubated overnight at a temperature of 2 to 8 degrees Celsius. During this time, the target analytes in the supernatant samples bind to the corresponding antibodies on each membrane.

After overnight incubation, each membrane is washed to remove any unbound material, and a detection antibody cocktail is added to each membrane. The membranes are subsequently incubated for one hour with a detection antibody cocktail. The detection antibody cocktail contains biotinylated detection antibodies that bind to each analyte captured on the membrane. Each membrane is washed to remove any unbound material, streptavidin-HRP is added to each membrane, and the membranes are incubated for half an hour. Streptavidin-HRP is a biotin-binding protein that binds to each detection antibody and provides signal amplification. Each membrane is again washed to remove any unbound material, a chemiluminescent detection reagent mix is added to each membrane, and the membranes are incubated for one minute. Any excess mix is squeezed out of each membrane.

The streptavidin-HRP catalyzes the chemical substrate in the chemiluminescent detection reagent mix and produces light as a by-product. The membranes are then developed (212) by exposing each membrane to X-ray film for 30 seconds to 10 minutes to capture the light signals produced on each membrane. The developed film (shown in FIG. 4A) shows positive signals corresponding to each analyte. Densitometry analysis is then performed (213) by collecting pixel densities corresponding to the signal strength of each analyte on each membrane and analyzing the pixel densities using a transmission-mode scanner and image analysis software. The relative pixel densities of each analyte on each membrane can be graphed on a histogram (shown in FIGS. 4B-4C), taking into account any background signal.

The histogram profile is subsequently analyzed, and analytes exhibiting pixel densities below a chosen threshold, such as 5000 average pixel density, are eliminated. Low pixel density is an indication of insignificant activity or background levels of an analyte, thus the activity of such an analyte should not be used to characterize differentiation. After low pixel density analytes are eliminated from further analysis (214), the data is further analyzed by comparing the pixel density data from key time points during differentiation to identify increasing, decreasing, or other changing trends, such as an increase or decrease just at a particular stage of differentiation, in analytes during differentiation (215). If the pixel density of an analyte does not exhibit an increasing, decreasing, or other changing trend throughout differentiation, that analyte is also eliminated from further analysis.

Once analytes with increasing or decreasing trends are identified by performing qualitative analysis (202), as shown in FIG. 2A, analytes of interest for characterization of differentiation are identified (203) for further analysis. In one example, all of the analytes that exhibit an increasing or decreasing trend based on the qualitative analysis can be further analyzed using quantitative analysis (204). In other examples, just the analytes exhibiting an increasing trend or those exhibiting a decreasing trend can be further analyzed. In other examples, a mix of analytes exhibiting increasing trends and decreasing trends can be further analyzed. In other examples, analytes exhibiting other changing trends, such as an increase or decrease just at a particular stage of differentiation, can be further analyzed. In yet other examples, a combination of anlaytes exhibiting increasing, decreasing, and/or other changing trends can be further analyzed.

Quantitative analysis is performed on the supernatant samples (204) to quantify trends in the analytes of interest. In one example, only analytes chosen based on qualitative analysis (202) are analyzed using quantitative analysis. In another example, qualitative analysis is not performed, and analytes chosen based on industry knowledge of the specific differentiation are analyzed using quantitative analysis. In another example, a combination of analytes chosen based on qualitative analysis (202) and/or analytes chosen based on industry knowledge are analyzed using quantitative analysis. Numerous methods for quantitative analysis may be used. In one example, a premixed multi-analyte kit, such as the Human Luminex® Screening Assay, may be used. In other examples, a printed array, enzyme-linked immunosorbent assay (ELISA), or mass spectrometry may be used. Quantitative analysis allows for comparison of actual concentration of analytes of interest in the supernatant samples, rather than relative comparison using a qualitative method (202). The concentration of analytes correlates to level of expression of the analytes throughout differentiation.

Figure 2C:
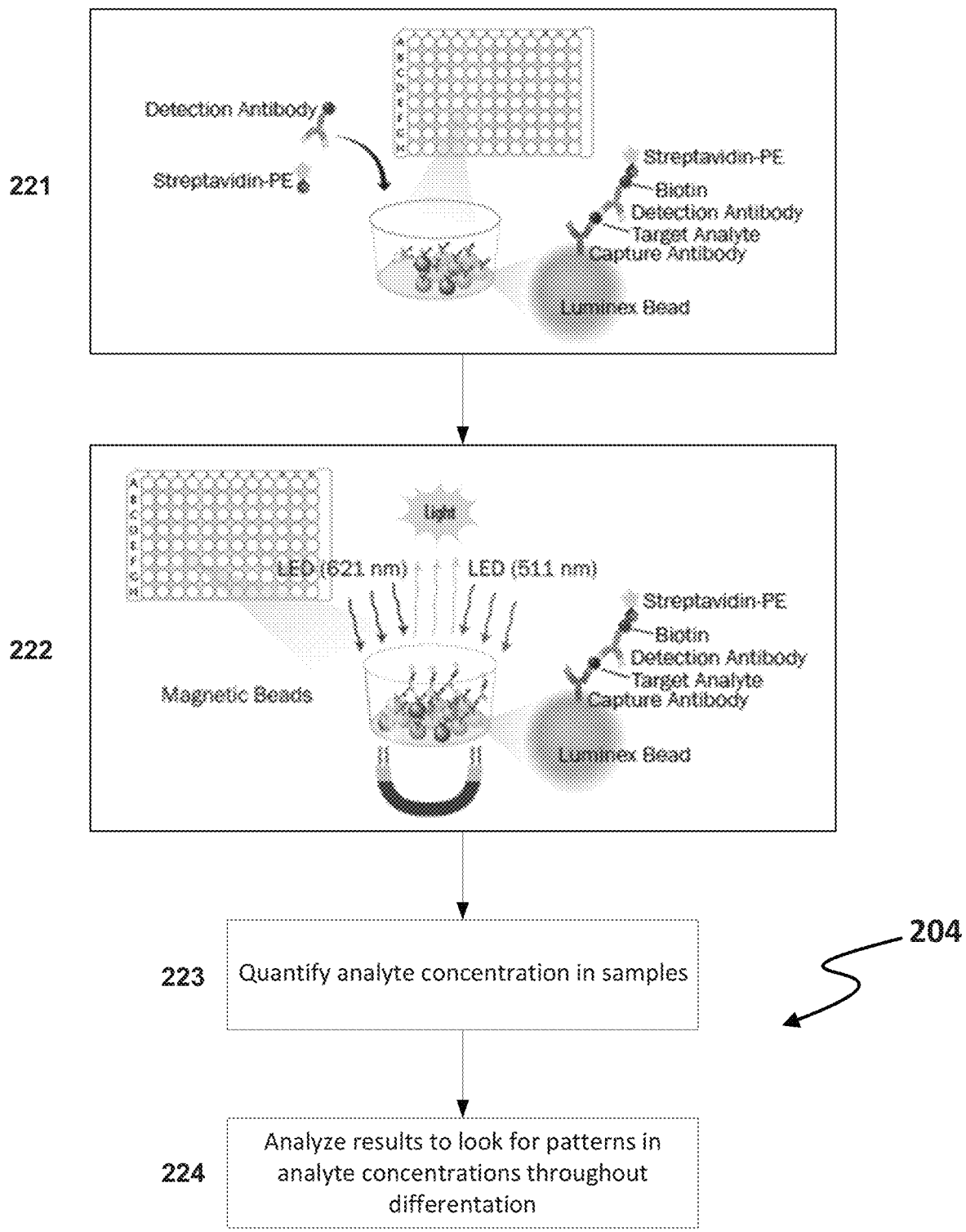
FIG. 2C is a flow diagram illustrating an example quantitative method for analyzing supernatant secretion profiles, used in the non-invasive profiling method of FIG. 2A.

FIG. 2C is a flow diagram illustrating quantitative method 204 for analyzing supernatant secretion profiles. In the example shown in FIG. 2C, method 204 is performed using the Human Luminex® Screening Assay, which can be used to assess the levels of up to 50 human biomarkers in a single supernatant sample. Quantitative analysis method 204 includes performing the assay protocol for supernatant samples from key time point throughout the differentiation (221), imaging the samples (222), quantifying the concentration of each analyte in the samples (223), and analyzing the results to look for patterns in analyte concentrations throughout the differentiation (224).

To perform the assay protocol (221), analyte-specific control and capture antibodies corresponding to analytes of interest are pre-coated onto color-coded magnetic microparticles (Luminex® beads). The microparticles, standards and samples are pipetted into wells of a 96-well plate and the immobilized antibodies bind the analytes of interest. In some examples, the supernatant samples can be diluted prior to addition to each well. In other examples, the supernatant samples are not diluted prior to addition to each well. Any unbound material is washed away, and a biotinylated antibody cocktail specific to the analytes of interest is added to each well. The biotinylated antibodies bind to corresponding analytes, and any unbound biotinylated antibody is washed away.

A streptavidin-phycoerythrin conjugate (Streptavidin-PE), which binds to the biotinylated antibody, is subsequently added to each well. A final wash removes unbound Streptavidin-PE, and the microparticles are resuspended in buffer. Streptavidin-PE can be excited with light to induce light emission that correlates to the concentration of biotinylated antibody. Thus, after the streptavidin-PE is added to each well, the wells are imaged (222) using, for example, the Luminex® MAGPIX® Analyzer. In this examples, a magnet in the analyzer captures and holds the superparamagnetic microparticles in a monolayer. Two spectrally distinct Light Emitting Diodes (LEDs) illuminate the samples, and the signals produced by the samples are detected with a charge-coupled device (CCD) camera. In other examples, the microparticles can be imaged with Luminex® 100/200™ or Bio-Rad® Bio-Plex® dual laser, flow-based sorting and detection systems.

In order to image the samples with the Luminex® MAGPIX® Analyzer, the samples are illuminated with one LED (621 nanometers) to identify the analyte that is being detected and a second second LED (511 nanometers) to determine the magnitude of the PE-derived signal, which is in direct proportion to the amount of analyte bound. The CCD camera detects the signals from the samples based on the first LED, and the signals are analyzed in order to classify the microparticles according to classify the microparticles based on the corresponding analyte-specific antibodies attached to those microparticles. The CCD camera subsequently detects signals from the samples based on the second LED. These signals are proportional to the amount of analyte bound to the analyte-specific antibodies. The signals are subsequently quantified to determine the concentration of each analyte in the samples (223). In one example, the signals can be compared to standard concentration curves for the analytes of interest to determine the concentration of each analyte based on a corresponding signal.

Histogram profiles can be generated (FIGS. 5A-5D) with concentration data from each analyte of interest for each key time point during the differentiation. The histogram profiles are subsequently analyzed to look for patterns in analyte concentrations throughout the differentiation. Once analyte trends are identified, as shown in FIG. 2A, these analyte trends can be used to characterize the differentiation (205).

The data can also be analyzed to predict differentiation success and/or optimize cell line specific differentiation protocols (206). For example, trends in certain analytes can be indicative of differentiation efficiency, success, or failure. The methods described with respect to FIGS. 2A-2C can be used to identify such analytes and modify differentiation protocols accordingly.

Figure 2D:
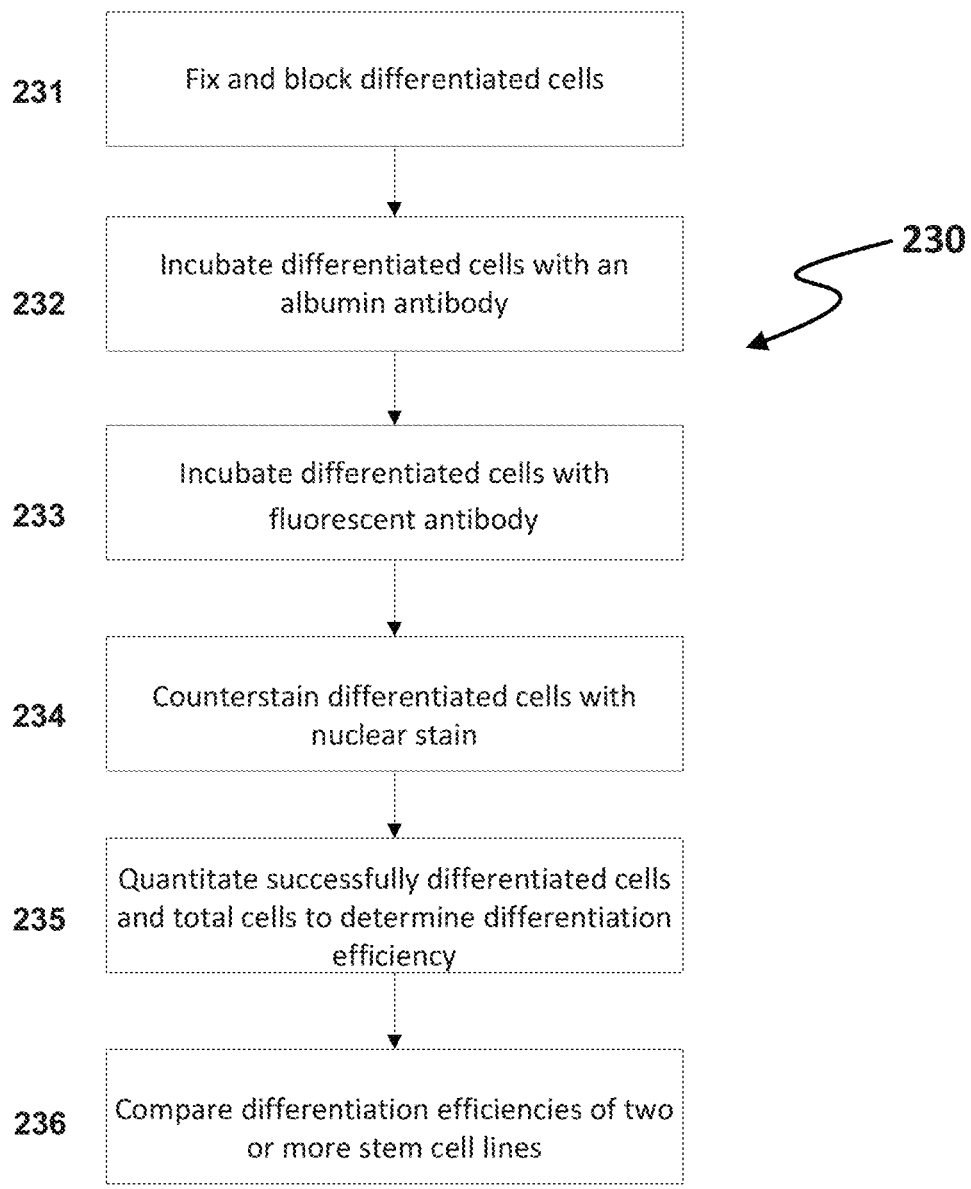
FIG. 2D is a flow diagram illustrating an example method for assessing differentiation efficiency.

The methods described in FIGS. 2A-2C can used to compare differentiations between two or more cell lines by comparing analyte concentrations and changes in concentrations throughout each differentiation. FIG. 2D is a flow diagram illustrating an example method 230 for assessing differentiation efficiency. In the example shown in FIG. 2D, method 230 is used to determine differentiation efficiency of stem cell differentiation into hepatocyte-like cells. In other examples, method 230 can be used to assess differentiation efficiency of any other cell resulting from differentiation. Method 230 includes fixing and blocking differentiated cells (231), incubating the cells with an albumin antibody (232), incubating the cells with a fluorescent secondary antibody (233), counterstaining the cells with nuclear stain (234), quantitating successfully differentiated cells and total cells to determine differentiation efficiency (235), and comparing differentiation efficiencies of two or more stem cell lines.

Once a differentiation is complete, the differentiated cells are fixed and blocked (231) by first fixing the cells with 4% paraformaldehyde in order to crosslink proteins and preserve the cells. The cells are subsequently washed to remove any excess material and subsequently blocked in a solution of 10% donkey serum, 1% bovine serum albumin (BSA), and 0.3% triton-x-100 in phosphate buffered saline (PBS). The blocking solution blocks non-specific binding and permeabilizes the cells to allow for entry of antibodies into the cells for binding. The cells are then incubated with a mouse anti-human albumin antibody (232). Albumin expression is one major characteristic of hepatocyte cells. Thus, albumin antibodies are used to identify cells that have successfully differentiated into hepatocyte-like cells. The albumin antibodies enter the cells and bind to those cells that are expressing albumin. The excess albumin antibodies are washed away.

After the albumin antibodies are bound, an anti-mouse secondary antibody conjugated to a fluorescent protein is added to the cells and the cells are incubated (233). The secondary antibodies bind to the albumin antibodies, and thus the fluorescent protein allows for fluorescent detection of cells expressing albumin. After the cells are incubated with the fluorescent protein, the cells are counterstained with a nuclear stain (234). In one example, the nuclear stain can be 4',6-diamidino-2-phenylindole (DAPI). The nuclear stain allows all of the cells, not just those expressing albumin, to be counted, so that differentiation efficiency can be determined.

Figure 3:
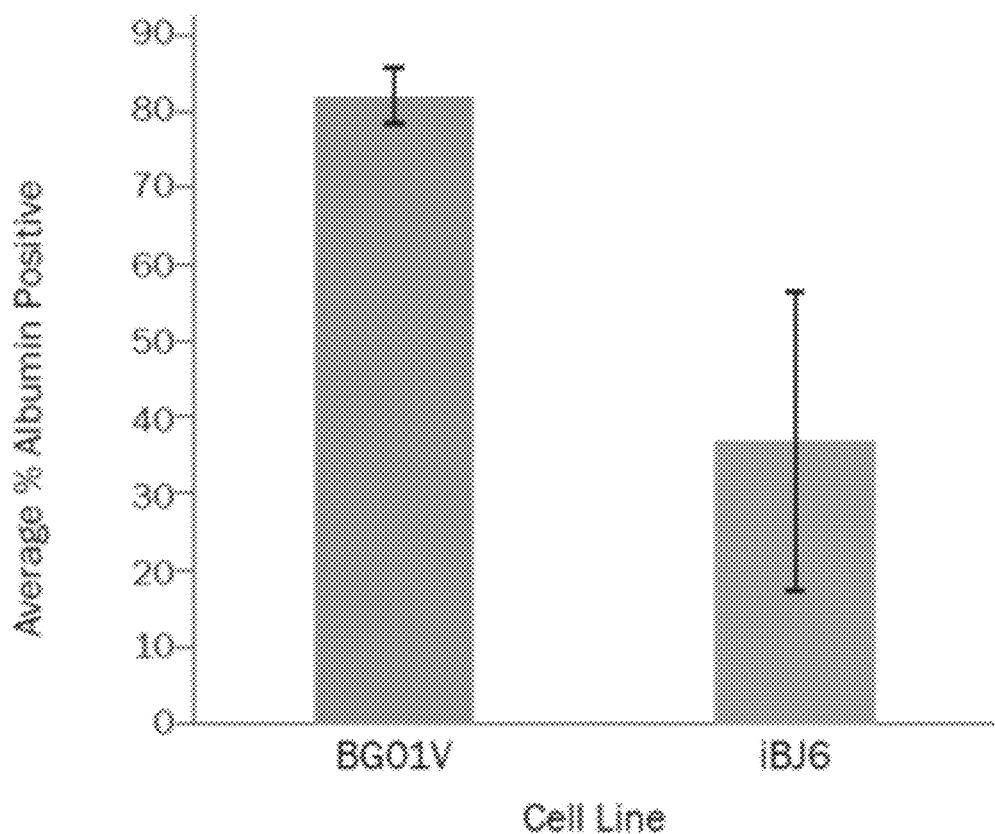
FIG. 3 is an example graph showing the differences in differentiation efficiency between a human embryonic stem (hES) cell line and a human induced pluripotent stem (hiPS) cell line.

Once the DAPI staining is complete, the successfully differentiated cells and total cells are quantitated (235). In one example, an Operetta High-Content Imaging System can be used to quantitate the successfully differentiated cells and total cells. This is done by looking at fluorescence intensity of the cells due to the presence of albumin and DAPI. User selected fluorescence intensity thresholds can be set to select for cells with a predetermined concentration of albumin indicative of successful differentiation. Once the albumin positive cells and total cells are quantified, differentiation efficiency is determined by comparing the quantity of cells positive for albumin staining in relation to the total number of cells (based on DAPI staining). This analysis can be performed on two or more stem cell lines, and the differentiation efficiency between the two can then be compared (236), as shown in FIG. 3 below.

The data obtained from the methods of FIGS. 2A-2C can be compared to the differentiation efficiencies of cell lines obtained using the method of FIG. 2D. This comparison can be used to determine whether trends in certain analytes are indicative of differentiation efficiency. This is advantageous, because such data could be instrumental in determining how to modify differentiation protocols to increase efficiency and success rates.

EXAMPLE 1

Figure 4A:
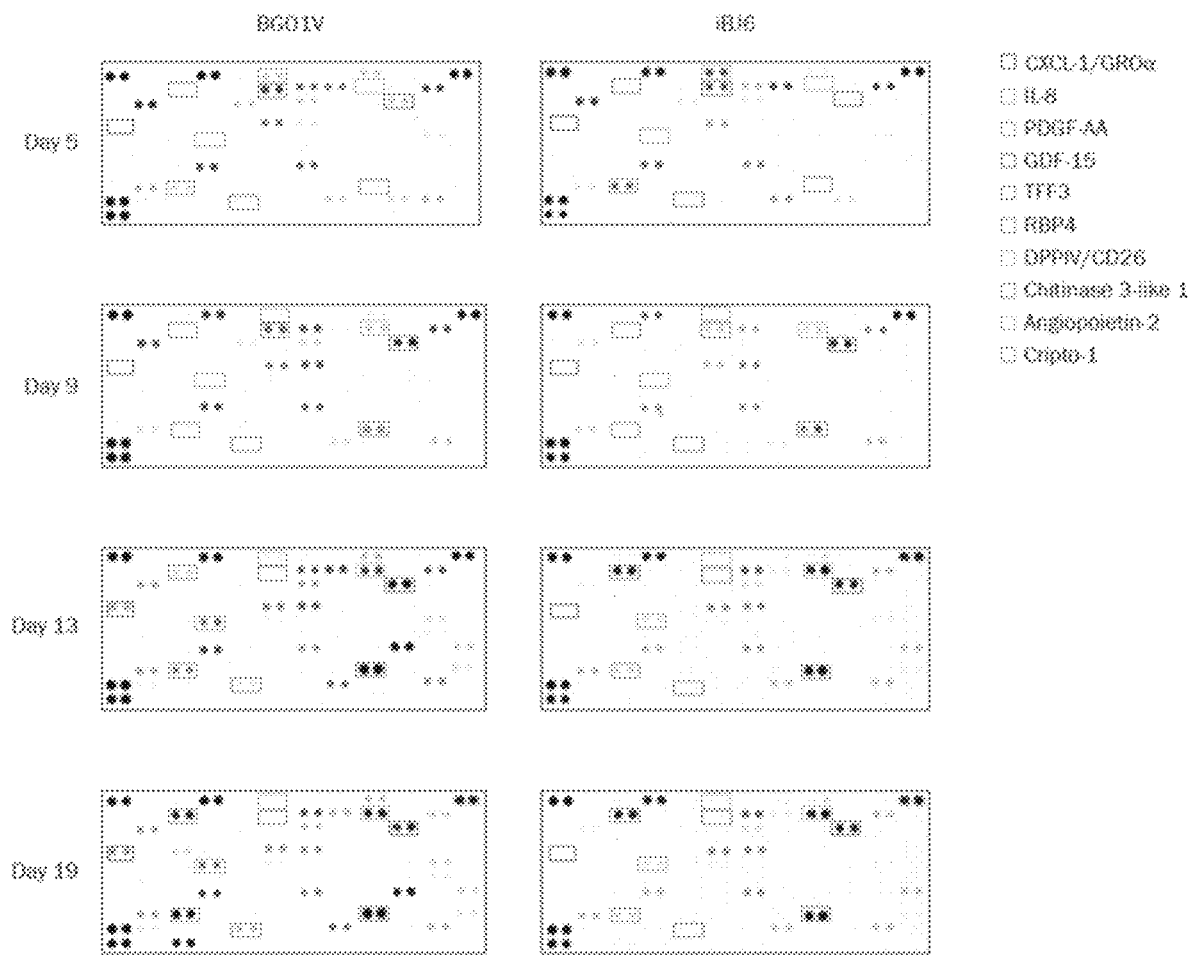
FIG. 4A is an example of antibody-based arrays used for qualitative analysis of analytes in supernatant samples from a hES cell line and a hiPS cell line.
Figure 4B:
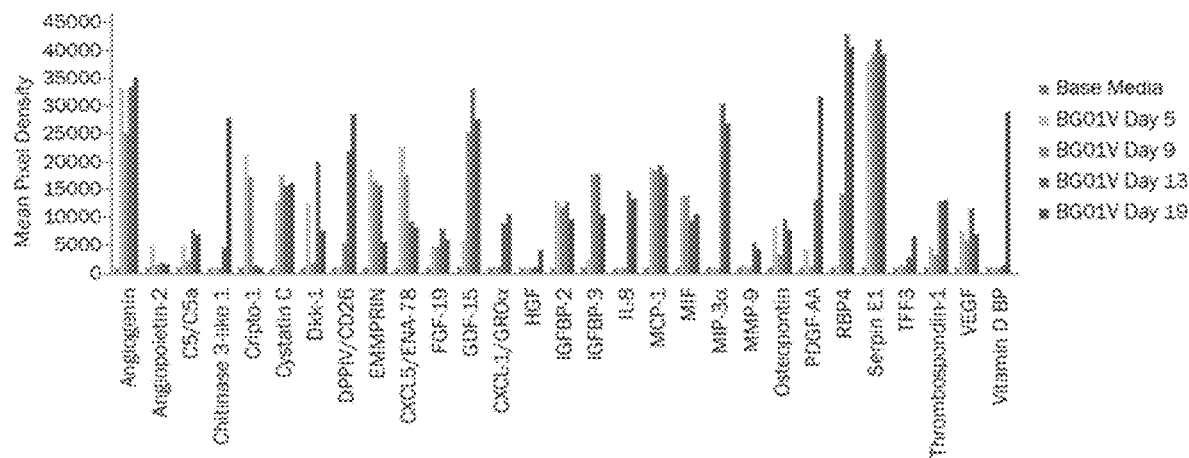
FIGS. 4B-4C are example histogram profiles of mean spot pixel density for select analytes of the arrays of FIG. 4A at key stages of differentiation in a hES cell line and a hiPS cell line.
Figure 4C:
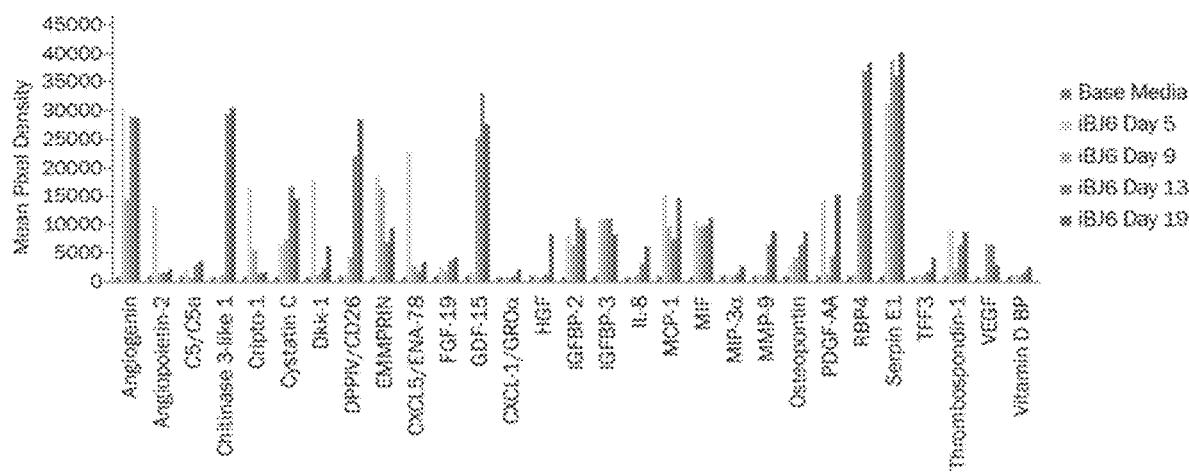

The methods of this disclosure were used to obtain cytokine and growth factor expression profiles from human induced pluripotent stem (hiPS) cell and human embryonic stem (hES) cell lines with known differences in hepatocyte differentiation efficiency. FIG. 3 is a graph showing the differences in efficiency between the two cell lines, BG01V hES cells and iBJ6 hiPS cells. BG01V and iBJ6 cells were differentiated into hepatocyte-like cells using the StemXVivo® Hepatocyte Differentiation Kit. Cell culture supernatant samples were taken on days 5, 9, 13, and 19 of the differentiation. The samples were analyzed qualitatively using the Proteome Profiler™ Human XL Cytokine Array Kit in order to obtain a secretion profile of the extracellular analytes in the supernatant. FIG. 4A shows arrays for both the BG01V and iBJ6 cells after the array was developed. FIGS. 4B-4C show histogram profiles of mean spot pixel density for select analytes in the arrays of FIG. 4A.

Figure 5A:
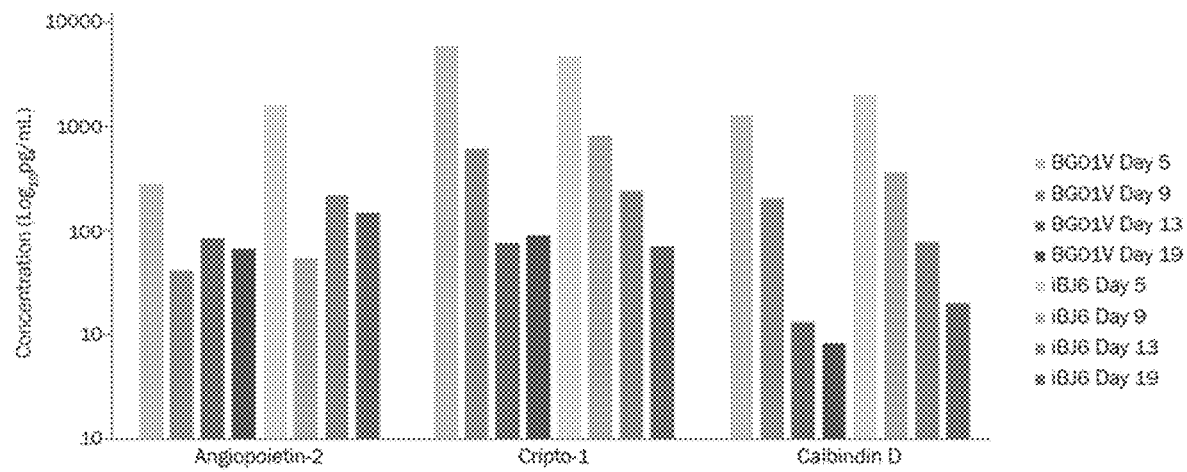
FIGS. 5A-5B are example histogram profiles of the concentration of analytes at key stages of differentiation in a hES cell line and a hiPS cell line.
Figure 5B:
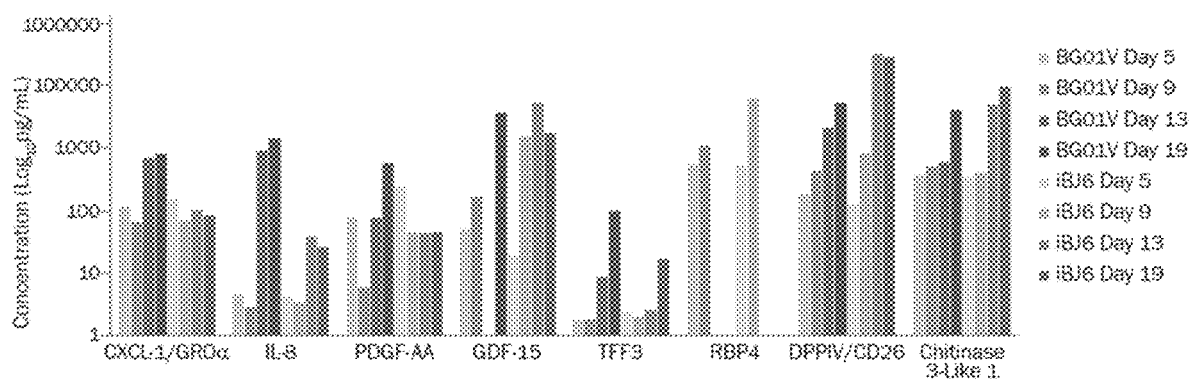
Figure 6A:
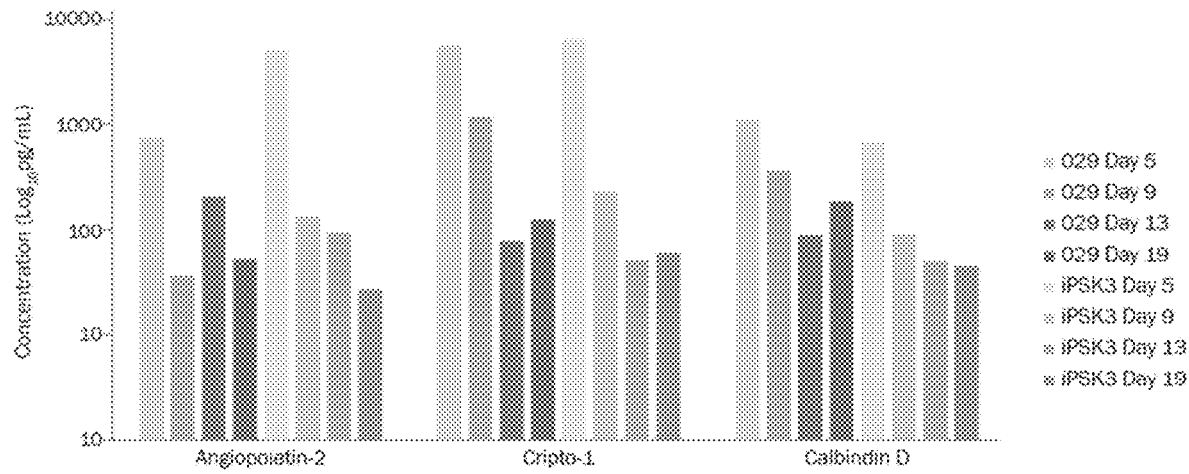
FIGS. 6A-6B are example histogram profiles of the concentration of analytes at key stages of differentiation in two different hiPS cell lines.
Figure 6B:
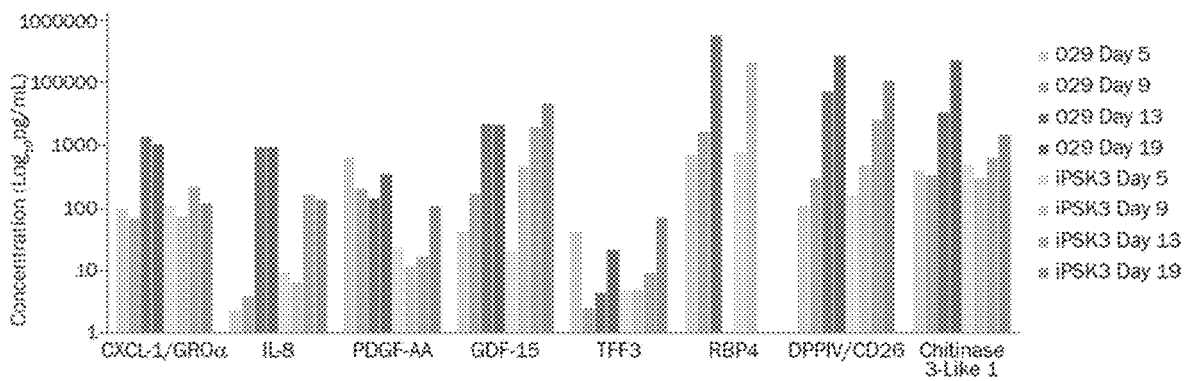

Analytes of interest were selected for both the BG01V and iBJ6 cells based on trends in analytes in the histogram profiles in FIGS. 4B-4C. The analytes of interest were subsequently quantitated using the Human Luminex® Screening Assay. FIGS. 5A-5B show the histogram profiles of the concentration of the analytes of interest. Two additional hiPS cell lines, 029 and iPSK3, were analyzed using the Human Luminex® Screening Assay to compare trends in the same analytes analyzed for the BG01V and iBJ6 cells. FIGS. 6A-6B show the histogram profiles of the concentration of the analytes of interest in the 029 and iPSK3 cells.

FIG. 3 is an example graph showing the differences in differentiation efficiency between the BG01V and iBJ6 cells. The differentiation efficiencies were obtained using albumin staining, which is described with respect to FIG. 3 above. As shown in FIG. 3, the BG01V cells have an approximately 80% differentiation efficiency while the iBJ6 cells have less than a 40% differentiation efficiency. Thus, the BG01V cell differentiation was almost twice as efficient as the iBJ6 cell differentiation. As described above, cell culture supernatant samples were taken from each of these cell lines on days 5, 9, 13, and 19 of the differentiation, and the samples were subsequently qualitatively and quantitatively analyzed for trends in analyte concentrations throughout the differentiation of both cell lines. The trends were analyzed to determine if there was a difference in analyte concentration between the two cell lines.

FIG. 4A shows antibody-based arrays used for qualitative analysis of analytes in supernatant samples from BG01V and iBJ6 cells. The arrays were obtained and analyzed using the Proteome Profiler™ Human XL Cytokine Array Kit according the method described with respect to FIG. 2B above. As shown in FIG. 4A (highlighted with the boxes), for both BG01V and iBJ6 cells, ten different analytes exhibited changes in expression throughout differentiation, including CXCL-1/GROα, IL-8, PDGF-AA, GDF-15, TFF3, RBP4, DPPIV/CD26, Chitinase 3-like 1, Angiopoietin-2, and Cripto-1. The relative pixel densities of these and additional analytes, along with pixel densities of the base media, were plotted on the histograms shown in FIGS. 4B-4C.

FIG. 4B is a histogram profile of mean pixel densities of secreted analytes from the BG01V cells on days 5, 9, 13, and 19 of the differentiation. FIG. 4C is a histogram profile of mean pixel densities of secreted analytes from the iBJ6 cells on days 5, 9, 13, and 19 of the differentiation. Based on these histogram profiles, any analytes with pixel densities below 5000 were eliminated as analytes of interest. From the remaining analytes, any analytes that did not exhibit changes in expression, either increasing or decreasing, throughout differentiation were also eliminated as analytes of interest. The remaining ten analytes, in addition to Calbindin D were quantitatively analyzed using the Human Luminex® Screening Assay according to the method described with respect to FIG. 2C above.

FIGS. 5A-5B are histogram profiles of concentrations of secreted analytes from the BG01V and iBJ6 cells on days 5, 9, 13, and 19 of differentiation. FIG. 5A shows a subset of analytes, including Angiopoietin-2, Cripto-1, and Calbindin D, which displayed decreasing levels throughout differentiation in both cell lines. FIG. 5B shows a subset of analytes, including CXCL-1/GROα, IL-8, PDGF-AA, GDF-15, TFF3, RBP4, DPPIV/CD26, and Chitinase 3-like 1, which displayed increasing levels throughout differentiation in both cell lines. As shown in FIGS. 5A-5B, the same analytes in both cell lines exhibited the same increasing or decreasing trends. Significant differences in analyte concentration or analyte trends between the two cell lines were not observed.

Based on the data in FIGS. 5A-5B, two additional hiPS cell lines, 029 and iPSK3 were differentiated into hepatocyte-like cells, and cell culture supernatants from days 5, 9, 13, and 19 were analyzed quantitatively using the Human Luminex® Screening Assay. FIGS. 6A-6B are histogram profiles of concentrations of secreted analytes from the 029 and iPSK3 cells on days 5, 9, 13, and 19 of differentiation. FIG. 5A shows a subset of analytes, including Angiopoietin-2, Cripto-1, and Calbindin D, which displayed decreasing levels throughout differentiation in both cell lines. FIG. 5B shows a subset of analytes, including CXCL-1/GROα, IL-8, PDGF-AA, GDF-15, TFF3, RBP4, DPPIV/CD26, and Chitinase 3-like 1, which displayed increasing levels throughout differentiation in both cell lines. The 029 and iPSK3 cells showed similar changes in analyte expression as those observed for BG01V and iBJ6 cells, as the same analyte subsets with decreasing and increasing trends were maintained in both cell lines.

While the analyte trends observed were not indicative of differences between differentiation efficiencies of the BG01V and iBJ6 cells, the methods of this disclosure can be used to identify additional analyte trends that could be indicative of differentiation efficiencies. The methods could also be used to develop methods for cell line specific optimization of differentiation protocols and/or methods for controlling the quality of the resulting cells prior to use of the cells in therapeutic applications.

EXAMPLE 2

Figure 7A:
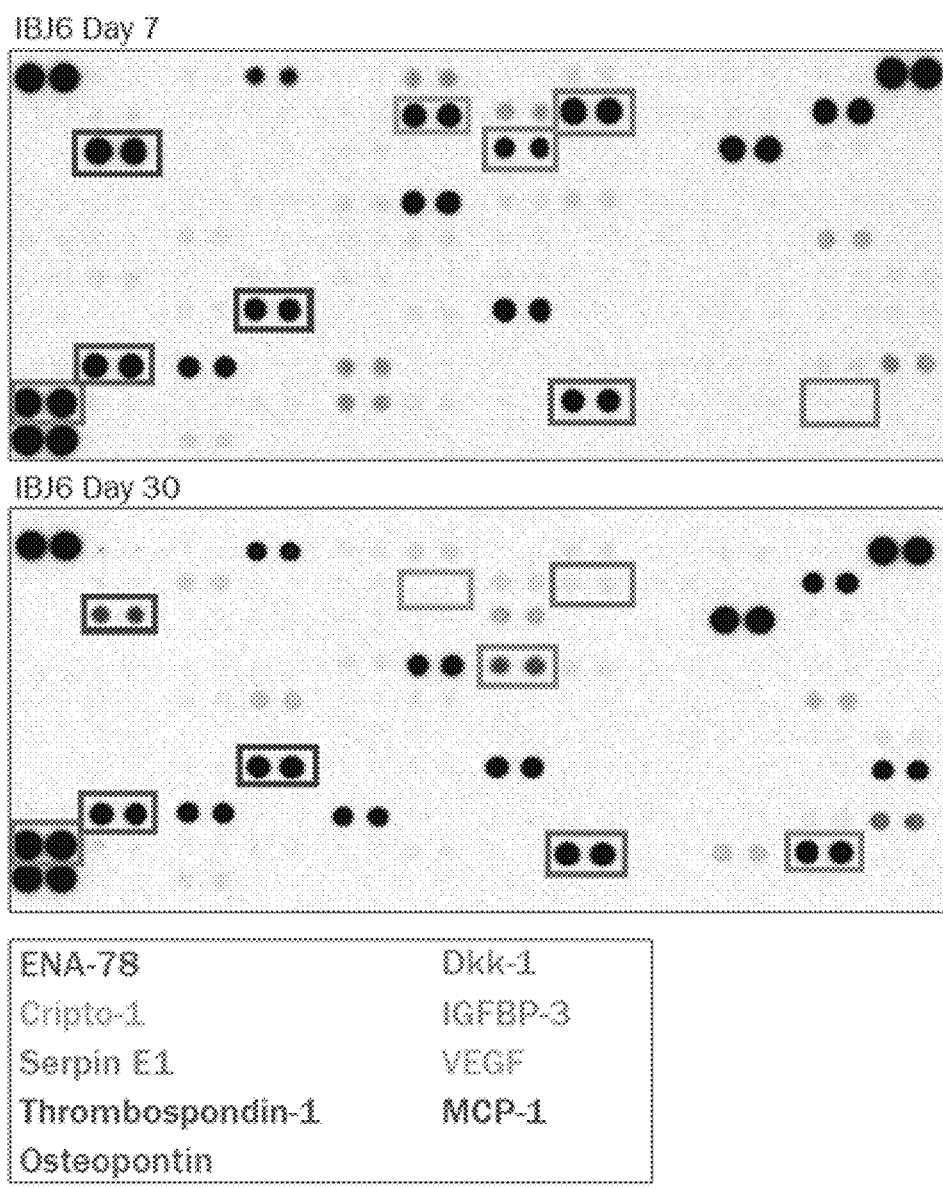
FIG. 7A is an example of antibody-based arrays used for qualitative analysis of analytes in supernatant samples from two different hiPS cell line.
Figure 7B:
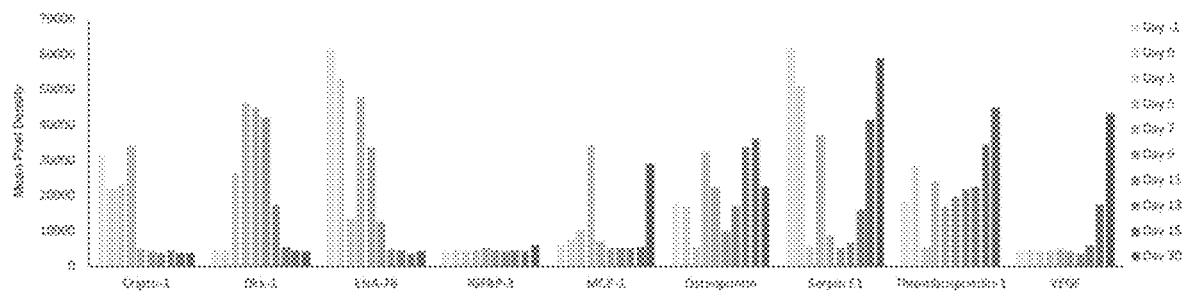
FIGS. 7B-7C are example histogram profiles of mean spot pixel density for select analytes of the arrays of FIG. 7A at key stages of differentiation in two different hiPS cell line.
Figure 7C:
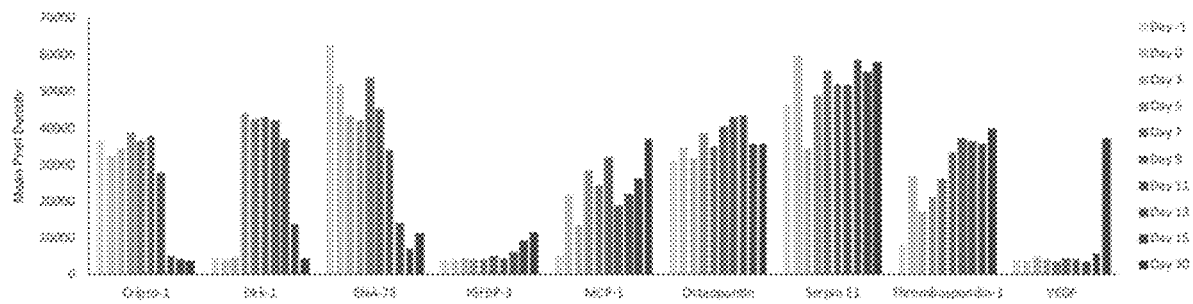

The methods of this disclosure were used to obtain cytokine and growth factor expression profiles from two different human induced pluripotent stem (hiPS) cell lines with known differences in cardiomyocyte differentiation efficiency, iBJ6 hiPS cells and JOY hIPS cells. iBJ6 and JOY cells were differentiated into cardiomyocyte cells using the StemXVivo® Cardiomyocyte Differentiation Kit. Cell culture supernatant samples were taken on days −1, 0, 3, 5, 7, 9, 11, 13, 15, and 30 of the differentiation. The samples were analyzed qualitatively using the Proteome Profiler™ Human XL Cytokine Array Kit in order to obtain a secretion profile of the extracellular analytes in the supernatant. FIG. 7A shows arrays for the iBJ6 cells after the array was developed. FIGS. 7B-7C show histogram profiles of mean spot pixel density for select analytes in the arrays of FIG. 7A for both iBJ6 and JOY cells.

Figure 8A:
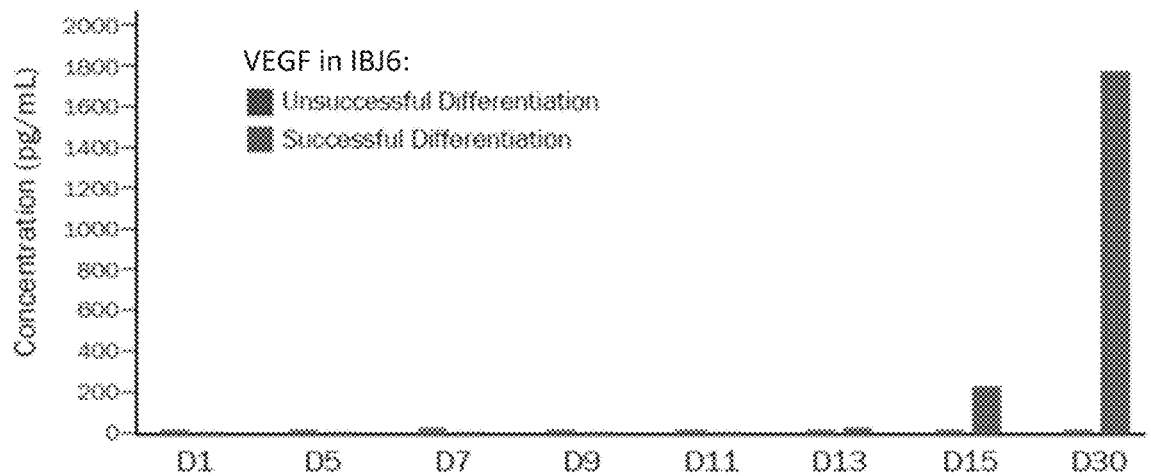
FIGS. 8A-8C are example histogram profiles of the concentration of analytes at key stages of differentiation in two different hiPS cell lines.
Figure 8B:
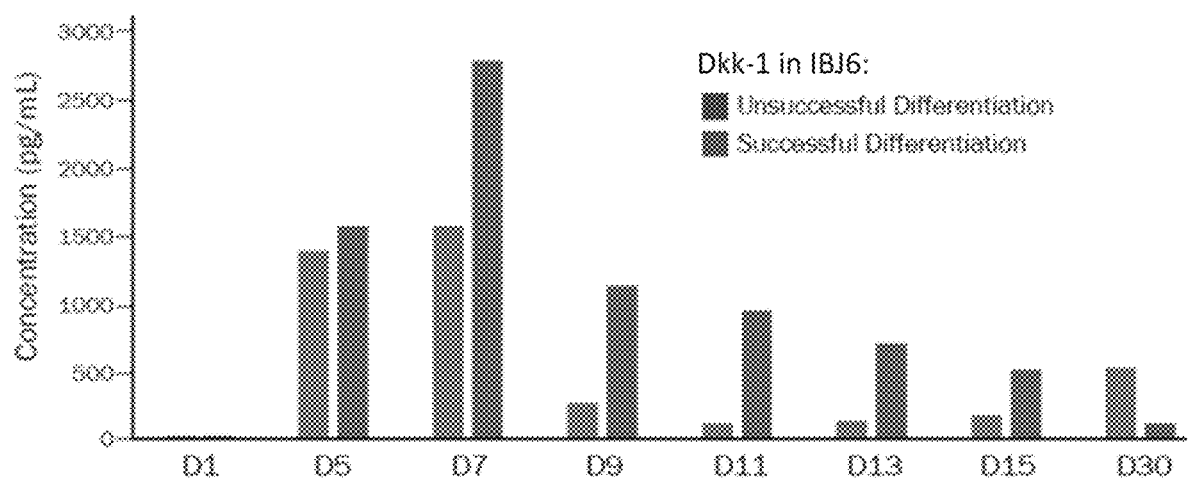
Figure 8C:
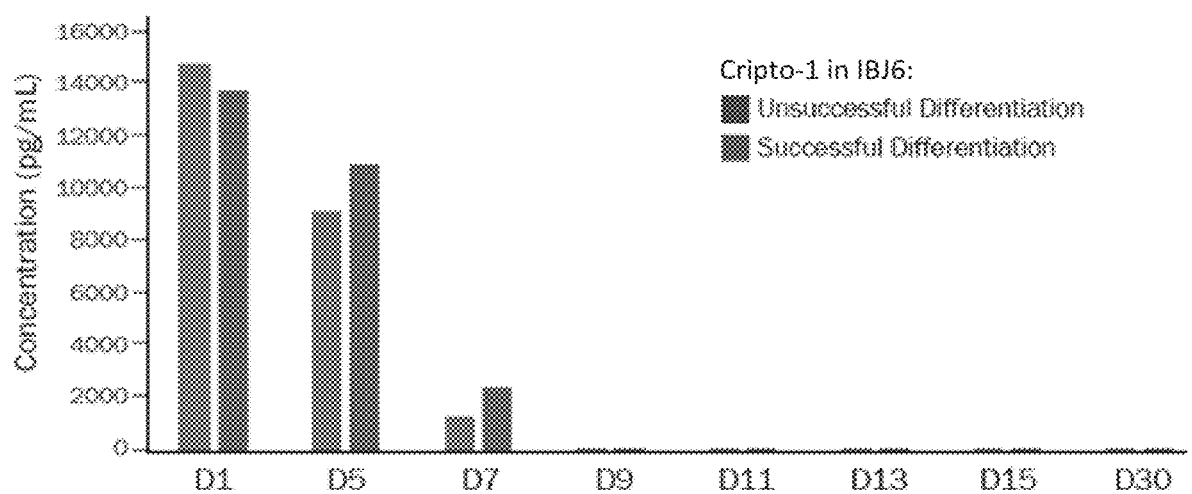

Analytes of interest were selected for iBJ6 cells based on trends in analytes in the histogram profiles in FIGS. 7B-7C. The analytes of interest were subsequently quantitated using the Human Luminex® Screening Assay. FIGS. 8A-8C show the histogram profiles of the concentration of the analytes of interest.

FIG. 7A shows antibody-based arrays used for qualitative analysis of analytes in supernatant samples from iBJ6 cells. The arrays were obtained and analyzed using the Proteome Profiler™ Human XL Cytokine Array Kit according to the method described with respect to FIG. 2B above. As shown in FIG. 7A (highlighted with the boxes), for both iBJ6 cells, nine different analytes exhibited changes in expression throughout differentiation, including Dkk-1, ENA-78, IGFBP-3, MCP-1, Osteopontin, Serpin E1, Thrombospondin-1, VEGF, and Cripto-1. The relative pixel densities of these analytes were plotted on the histograms shown in FIGS. 7B-7C.

FIG. 7B is a histogram profile of mean pixel densities of secreted analytes from the iBJ6 cells on days −1, 0, 3, 5, 7, 9, 11, 13, 15, and 30 of the differentiation. FIG. 7C is a histogram profile of mean pixel densities of secreted analytes from the JOY cells on days −1, 0, 3, 5, 7, 9, 11, 13, 15, and 30 of the differentiation. Based on these histogram profiles, MCP-1, Osteopontin, Serpin E1, Thrombospondin-1, and VEGF were identified as analytes that increased during differentiation in both iBJ6 and JOY cells. Cripto-1 and ENA-78 were identified as analytes that decreased during differentiation and Dkk-1 was identified as an analyte that had varied expression during differentiation in both iBJ6 and JOY cells. IGFBP-3 had pixel densities below 5000 in both iBJ6 and JOY cells, so it was eliminated as an analyte of interest.

Selected analytes from the qualitative analysis, including VEGF, Dkk-1, and Cripto-1, were quantitatively analyzed using the Human Luminex® Screening Assay according to the method described with respect to FIG. 2C above. These analytes were analyzed in the context of successful cardiomyocyte differentiations (>75% beating cardiomyocytes at differentiation day 15) and unsuccessful differentiations (<20% beating cardiomyocytes are differentiation day 15).

FIGS. 8A-8C are histogram profiles of concentrations of secreted analytes from successful and unsuccessful differentiations of iBJ6 cells on days 1, 5, 7, 9, 11, 13, 15, and 30 of differentiation. FIG. 8A shows the concentration of VEGF, which displayed increasing levels throughout successful differentiation and minimal change in levels throughout unsuccessful differentiation. FIG. 8B shows the concentration of Dkk-1, which displayed higher levels on days 5, 7, 9, 1, 13, and 15 in successful differentiation as compared to unsuccessful differentiation, and a lower level on day 30 in successful differentiation as compared to unsuccessful differentiation. FIG. 8C shows the concentration of Cripto-1, which displayed decreasing levels throughout successful and unsuccessful differentiation. FIGS. 8A-8C show that expression of VEGF and Dkk-1 vary between successful and unsuccessful differentiation experiments.

The invention claimed is:

1. A method for profiling stem cell differentiation, the method comprising:
   harvesting differentiation media supernatant containing secreted analytes at a plurality of key time points during a stem cell differentiation, wherein two or more of the plurality of key time points are separated by at least two days;
   performing an analysis of the differentiation media supernatant with respect to at least one secreted analyte, wherein the at least one secreted analyte comprises RBP4, wherein the analysis comprises a qualitative analysis or a quantitative analysis or both a qualitative analysis and a quantitative analysis; and
   identifying a trend in analyte expression based on the analysis of the differentiation media supernatant, wherein a trend comprises an increase or a decrease in a level of a secreted analyte between key time points.

2. The method of claim 1, wherein the stem cell differentiation is a differentiation of a pluripotent stem cell into a hepatocyte-like cell or a cardiomyocyte.

3. The method of claim 2, wherein the pluripotent stem cell is a human embryonic stem cell.

4. The method of claim 2, wherein the pluripotent stem cell is a human induced pluripotent stem cell.

5. The method of claim 1, wherein the at least one secreted analyte further comprises a secreted analyte selected from the group consisting of CXCL-1/GROα, IL-8, PDGF-AA, GDF-15, TFF3, DPPIV/CD26, Chitinase 3-like 1, Angiopoeietin-2, Cripto-1, Calbindin D, Dkk-1, ENA-78, IGFBP-3, MCP-1, Osteopontin, Serpin E1, Thrombospondin-1, and VEGF.

6. The method of claim 1, wherein performing the qualitative analysis comprises:
   providing an antibody-based array including at least one antibody for capturing the at least one secreted analyte for analysis;
   capturing light signals from the antibody-based array on x-ray film, the light signals corresponding to expression of the at least one secreted analyte;
   performing densitometry analysis on the signals captured on the x-ray film; and
   plotting the pixel densities for each the at least one secreted analyte for each of the plurality of key time points.

7. The method of claim 1, wherein performing the quantitative analysis comprises:
   providing an antibody-based screening assay including at least one antibody for capturing the at least one secreted analyte for analysis;
   illuminating the antibody-based screening assay with light and detecting a signal from the antibody-based screening assay corresponding to each of the plurality of key time points;
   quantifying the signal from the antibody-based assay to determine a concentration of the at least one secreted analyte for each of the plurality of key time points; and
   plotting the concentration of the at least one secreted analyte for each of the plurality of key time points.

8. A method for profiling stem cell differentiation, the method comprising:
   harvesting differentiation media supernatant containing secreted analytes at a plurality of key time points during a stem cell differentiation of a pluripotent stem cell into a hepatocyte-like cell or a cardiomyocyte, wherein two or more of the plurality of key time points are separated by at least two days;

performing an analysis of the differentiation media supernatant with respect to at least one secreted analyte, wherein the at least one secreted analyte comprises RBP4, wherein the analysis comprises a qualitative analysis or a quantitative analysis or both a qualitative analysis and a quantitative analysis; and identifying a trend in analyte expression based the analysis of the differentiation media supernatant, wherein a trend comprises an increase or a decrease in a level of a secreted analyte between key time points.

9. The method of claim 8, wherein the pluripotent stem cell is a human embryonic stem cell.

10. The method of claim 8, wherein the pluripotent stem cell is a human induced pluripotent stem cell.

11. The method of claim 8, further comprises a secreted analyte selected from the group consisting of CXCL-1/GROα, IL-8, PDGF-AA, GDF-15, TFF3, DPPIV/CD26, Chitinase 3-like 1, Angiopoeietin-2, Cripto-1, Calbindin D, Dkk-1, ENA-78, IGFBP-3, MCP-1, Osteopontin, Serpin E1, Thrombospondin-1, and VEGF.

12. The method of claim 8, wherein performing the qualitative analysis comprises:
providing an antibody-based array including at least one antibody for capturing the at least one secreted analyte for analysis;
capturing light signals from the antibody-based array on x-ray film, the light signals corresponding to expression of the at least one secreted analyte;
performing densitometry analysis on the signals captured on the x-ray film; and
plotting the pixel densities for each the at least one secreted analyte for each of the plurality of key time points.

13. The method of claim 8, wherein performing the quantitative analysis comprises:
providing an antibody-based screening assay including at least one antibody for capturing the at least one secreted analyte for analysis;
illuminating the antibody-based screening assay with light and detecting a signal from the antibody-based screening assay corresponding to each of the plurality of key time points;
quantifying the signal from the antibody-based assay to determine a concentration of the at least one secreted analyte for each of the plurality of key time points; and
plotting the concentration of the at least one secreted analyte for each of the plurality of key time points.

14. A method for profiling stem cell differentiation, the method comprising:
harvesting differentiation media supernatant containing secreted analytes at a plurality of key time points during a stem cell differentiation, wherein two or more of the plurality of key time points are separated by at least two days;
performing a qualitative analysis of the differentiation media supernatant with respect to at least one secreted analyte;
identifying at least one analyte of interest, wherein the at least one analyte of interest comprises RBP4;
performing a quantitative analysis of the differentiation media with respect to the at least one analyte of interest; and
identifying a trend in analyte expression in the differentiation media supernatant based on the qualitative analysis or the quantitative analysis or both, wherein a trend comprises an increase or a decrease in a level of a secreted analyte between key time points.

15. The method of claim 14, wherein the stem cell differentiation is a differentiation of a pluripotent stem cell into a hepatocyte-like cell or a cardiomyocyte.

16. The method of claim 15, wherein the pluripotent stem cell is a human embryonic stem cell.

17. The method of claim 15, wherein the pluripotent stem cell is a human induced pluripotent stem cell.

18. The method of claim 14, wherein the at least one analyte of interest further comprises a secreted analyte selected from the group consisting of CXCL-1/GROα, IL-8, PDGF-AA, GDF-15, TFF3, DPPIV/CD26, Chitinase 3-like 1, Angiopoeietin-2, Cripto-1, Calbindin D, Dkk-1, ENA-78, IGFBP-3, MCP-1, Osteopontin, Serpin E1, Thrombospondin-1, and VEGF.

19. The method of claim 14, wherein performing the qualitative analysis comprises:
providing an antibody-based array including at least one antibody for capturing the at least one secreted analyte for analysis;
capturing light signals from the antibody-based array on x-ray film, the light signals corresponding to expression of the at least one secreted analyte;
performing densitometry analysis on the signals captured on the x-ray film; and
plotting the pixel densities for each the at least one secreted analyte for each of the plurality of key time points.

20. The method of claim 14, wherein performing the quantitative analysis comprises:
providing an antibody-based screening assay including at least one antibody for capturing the at least one secreted analyte for analysis;
illuminating the antibody-based screening assay with light and detecting a signal from the antibody-based screening assay corresponding to each of the plurality of key time points;
quantifying the signal from the antibody-based assay to determine a concentration of the at least one secreted analyte for each of the plurality of key time points; and
plotting the concentration of the at least one secreted analyte for each of the plurality of key time points.

* * * * *